(12) United States Patent
Miyasaka et al.

(10) Patent No.: US 6,258,252 B1
(45) Date of Patent: Jul. 10, 2001

(54) METHOD OF ANALYZING CORROSION AND CORROSION PREVENTION

(75) Inventors: Matsuho Miyasaka, Yokohama; Hirokazu Takayama, Tokyo; Kenji Amaya, Kawasaki; Shigeru Aoki, Yokohama, all of (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 09/115,694

(22) Filed: Jul. 15, 1998

(30) Foreign Application Priority Data

Jul. 16, 1997 (JP) .................................................... 9-207186

(51) Int. Cl.$^7$ .................................................. G01N 17/04
(52) U.S. Cl. .......................................................... 205/775.5
(58) Field of Search ................................... ; G01N 17/04

(56) References Cited

U.S. PATENT DOCUMENTS 5,508,945 * 4/1996 Mizoh et al. ......................... 364/563

FOREIGN PATENT DOCUMENTS 0 466 386   1/1992 (EP) .

OTHER PUBLICATIONS

M. Miyasaka, et al., Tabo Kikai (Turbomachinery), vol. 23, No. 10, "Corrosion Protection Design of Seawater Pump Using Boundary Element Analysis", 1995, (English Abstract Only) No month available.

M. Iwata, et al., Journal of the Society of Naval Architects of Japan, vol. 174, pp. 777–786, "BEM Analysis of the Potential Distribution on a Tubular Structure Under Cathodic Protection", 1993 No month available.

K. Amaya, et al., Nippon Kikai Gakkai Keisan Rikigaku Koenkai Koen Ronbunshu, pps. "Parameter Estimation of Human Locomotion Model", 1997, (English Abstract Only) No month available.

R.S. Munn, et al., Corrosion, vol. 47, No. 8, pp. 618–634, "Numerical Modeling and Solution of Galvanic Corrosion Systems: Part II. Finite–Element Formulation and Descriptive Examples", Aug., 1991.

S.H. Lee, et al., Journal of Computational Physics, vol. 107, No. 2, pp. 338–347, "A Boundary Element Model of Cathodic Well Casing Protection", Aug., 1993.

M. Miyasaka, et al., Zairyo to Kankyo (Corrosion Engineering), vol. 44, No. 4, "Boundary Element Analysis on Cathodic Protection of Seawater Pump", Apr. 15, 1997, (English Abstract Only).

Y. Kurata, Tohoku Koken Nyusu, "Galvanic Corrosion of a Carbon Steel/Stainless Steel Couple in Water Solution Saturated with CO2–NaCl", Jul. 1, 1996, (English Abstract Only).

M.W. Verbrugge, Journal of Electrostatics, vol. 34, No. 1, pps. 61–85, "Primary Current Distribution in a Thin–Film Battery Application to Power–Density Calculations for Lithium Batteries", Feb., 1995.

J. Fleig, et al., Solid State Ionics, vol. 94, No. 1, pps. 199–207, "Rough Electrodes in Solid and Liquid Electrochemistry: Impact of Morphology on the Impedance", Feb. 1, 1997.

Matsuho Miyasaka, et al., "A Boundary Element Analysis on Galvanic Corrosion Problems—Computational Accuracy on Galvanic Fields With Screen Plates", Corrosion Science, vol. 30, No. 2/3, (1990), p. 299–311. No month available.

Strommen, R.D. "Computer Modeling of Offshore Cathodic Protection Systems: Method and Experience", Computer Modeling in Corrosion, Astmstp1154, R.S. Munn, Ed., American Society for Testing and Materials, Philadelphia (1992), p. 229–247. No month available.

* cited by examiner

Primary Examiner—Bruce F. Bell
(74) Attorney, Agent, or Firm—Oblon, Spivak, McClelland, Maier & Neustadt, P.C.

(57) ABSTRACT

An object to be analyzed for corrosion and corrosion prevention is divided into a plurality of adjacent regions of plural types by a dividing plane, with one of the adjacent regions being referred to as an attentional region with a boundary as the dividing plane and the other as a non-attentional region with a boundary as the dividing plane. An initial current density or an initial potential is imparted to each element of the boundary of the non-attentional region to effect a boundary element analysis for determining a relationship between a potential and a current density in each the element. A potential distribution and a current density distribution in the attentional region in its entirety are determined, using the relationship between the potential and the current density in each the element of the boundary of the non-attentional region as a boundary condition for the attentional region.

5 Claims, 7 Drawing Sheets

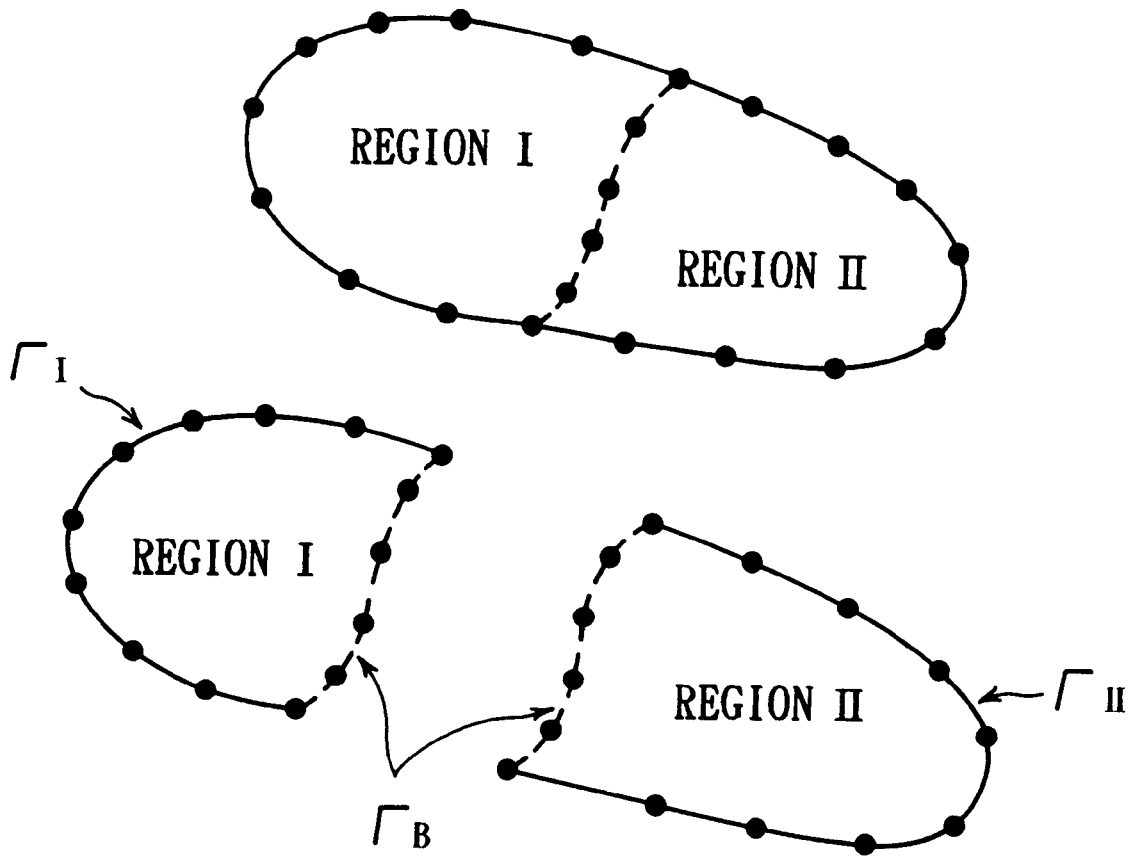
F I G. 2

F I G. 3
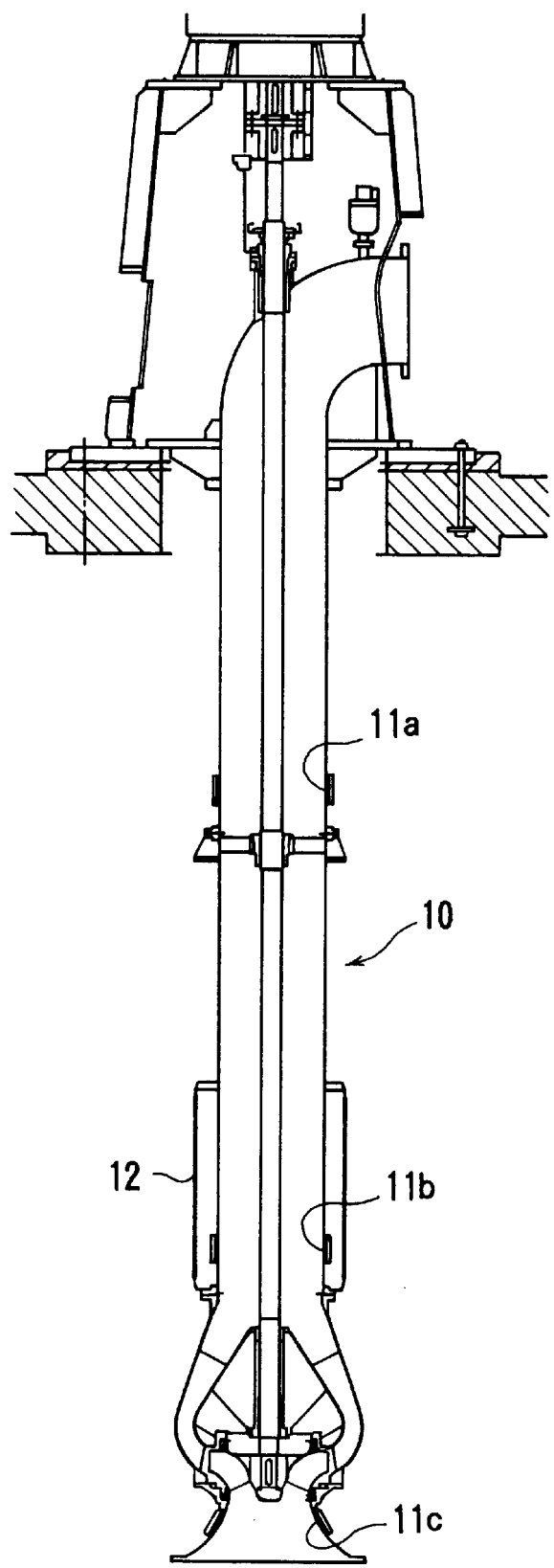

F I G. 4
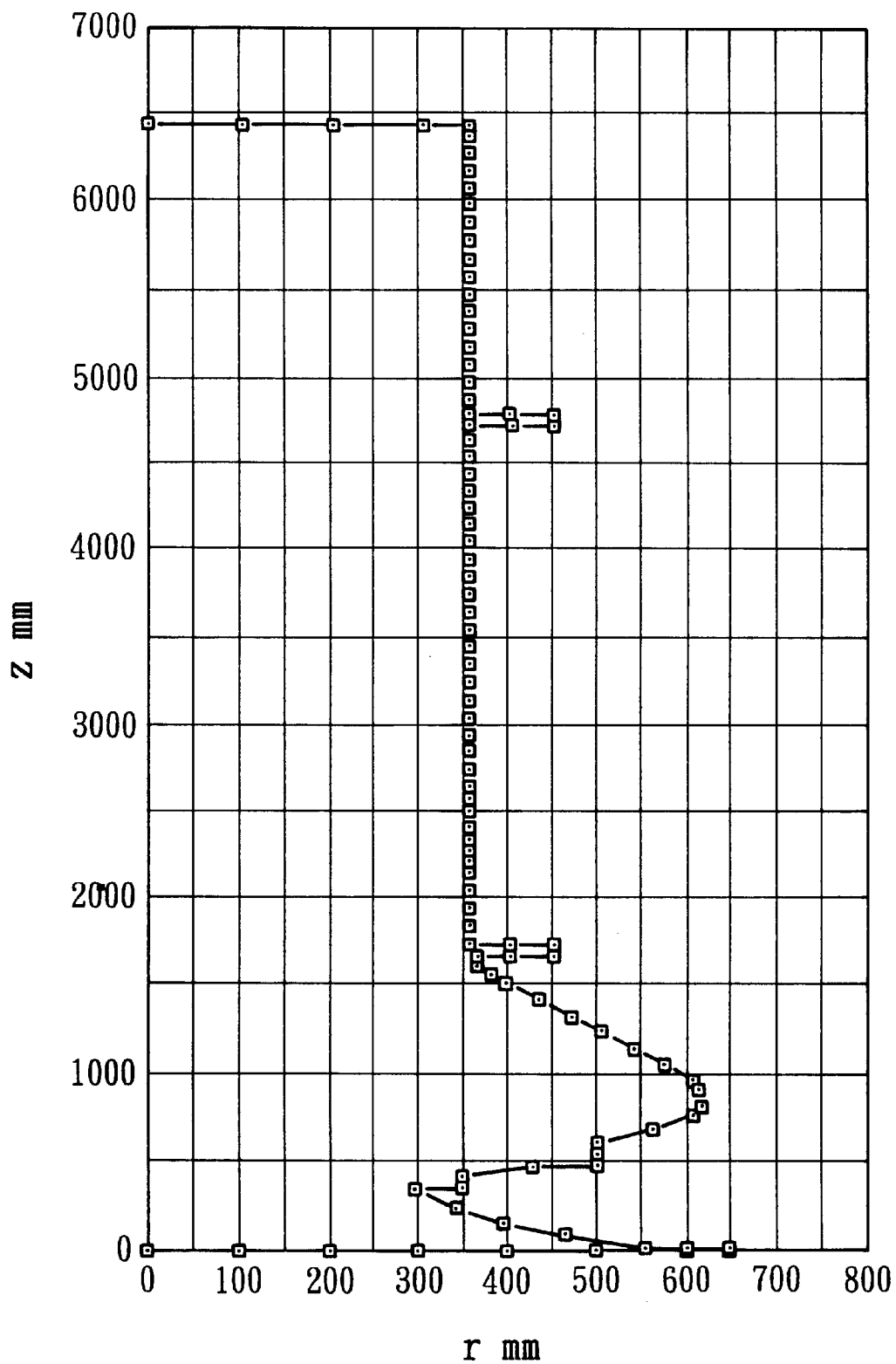

FIG. 8A
FIG. 8B
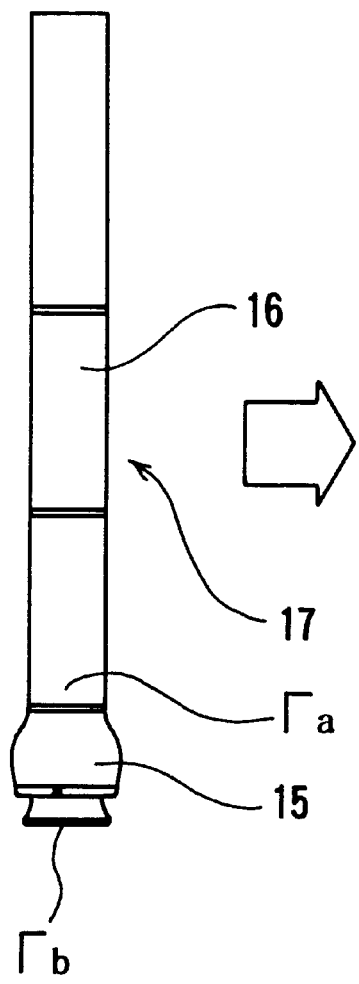
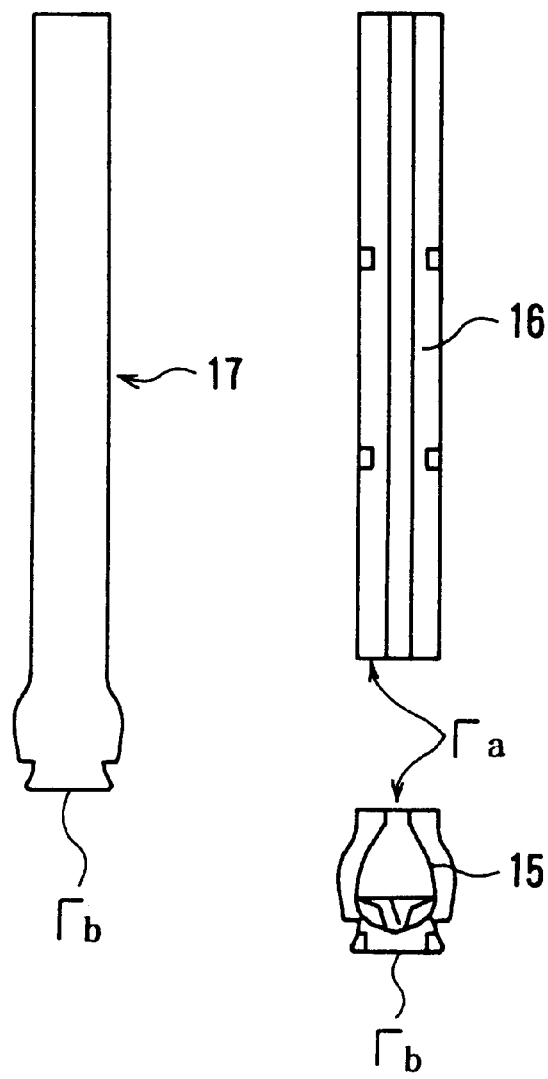

METHOD OF ANALYZING CORROSION AND CORROSION PREVENTION

BACKGROUND OF THE INVENTION

1. Field of the Invention

The present invention relates to a method of effecting a computerized analysis for predicting corrosion and corrosion prevention of metals, and more particularly to a method of analyzing macro cell corrosion such as bimetallic corrosion (also referred to as "galvanic corrosion") and differential aeration corrosion and cathodic corrosion prevention, among various metal corrosion and corrosion prevention phenomena. The present invention is also concerned with an analytical method applicable to a system such a plating system, a battery, an electrolytic tank, etc. where a macro anode and a macro cathode exist across an electrolyte, developing a field of electric potential.

2. Description of the Prior Art

In solutions having high electric conductivity, such as seawater, metals are susceptible to macro cell corrosion such as bimetallic corrosion caused when different metals are used together or differential flow velocity corrosion, i.e., differential aeration corrosion, due to flow velocity distribution irregularities. It has been desired to predict those corrosions accurately in advance so that appropriate preventive measures can be taken. Cathodic corrosion prevention based on the positive use of a corrosion inhibiting phenomenon at a cathode in a macro cell is finding wide use as the most basic corrosion prevention process. There has been a demand for the prediction of a range of corrosion prevention and the rate of consumption of a sacrificial anode depending on the material of the anode, the position of installation of the anode, the shape and materials of devices to be protected against corrosion, and solution conditions including electric conductivity, flow velocity, etc.

Experimental approaches to the precision analysis of macro cell corrosion suffer limitations because the configuration of the field has a large effect on the behavior of macro cells. Specifically, when an experiment is conducted on bimetallic corrosion to inspect in detail the effect of various factors including the ratio of areas, the combination of materials, and the electric conductivity of the solution, the experimental result applies only to the three-dimensional shape of a region occupied by the solution in the experiment. Since actual devices and structures are quite complex in shape, the liquid junction resistance in a macro cell cannot accurately be estimated, and the experimental result cannot apply directly to the actual situation. It is practically impossible to carry out an experiment on the particular shape of a device to be protected against corrosion each time the shape of the device is changed. For these reasons, it has heretofore customary to predict macro cell corrosion and cathodic corrosion prevention for actual structures mostly according to empirical rules.

Many attempts have been made to achieve a more accurate and quantitative analysis of macro cell corrosion and cathodic corrosion prevention for actual structures. One effort has been to solve purely mathematically a Laplace's equation governing a potential distribution for determining a potential distribution and a current density distribution. Objects to be analyzed by this process are limited to relatively simple systems in the form of flat plates, cylinders, etc. Processes long known in the art for analyzing electric field problems including a conformal mapping process and a process using electrically conductive paper. These processes, however, handle two-dimensional fields only.

With the development in recent years of the computer technology, various efforts have been made to apply numerical analyses using a difference method, a finite element method, and a boundary element method. The difference method and the finite element method are disadvantageous in that the time required for calculations is very long because an object to be handled needs to be divided into elements. According to the boundary element method, since only the surface of an object to be handled needs to be divided into elements, it is possible to greatly reduce the time required to divide the object into elements and the time required for calculations. Based on the belief that the boundary element method is most suitable for analyzing corrosion problems where physical quantities including a potential and a current density on a surface are important, the inventors have developed an analytical technique based on the boundary element method for the prediction of macro cell corrosion and cathodic corrosion prevention problems.

Basic Equations and Boundary Conditions

The corrosion of a metal in an aqueous solution develops due to electrochemical reactions which comprise a pair of anodic and cathodic reactions. For example, the reactions which corrode iron in an aqueous solution of neutral salt, such as seawater, proceed according to the following equations (1) and (2):

$$\mathrm{Fe} \rightarrow \mathrm{Fe}^{2+} + 2e^- \text{(anodic reaction)} \tag{1}$$

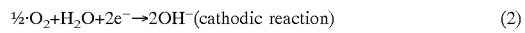

$$\tfrac{1}{2} \mathrm{O}_2 + \mathrm{H}_2\mathrm{O} + 2e^- \rightarrow 2\mathrm{OH}^- \text{(cathodic reaction)} \tag{2}$$

On a surface of metal, an area where an anodic reaction occurs is referred to as anode, and an area where a cathodic reaction occurs is referred to as cathode. With respect to the corrosion of iron in seawater, anodes and cathodes are usually very small and mixed together, and their positions are not fixed. Therefore, the corrosion progresses substantially uniformly over the entire surface while producing some surface irregularities. If the material, the surface state, and the environment are not uniform, then anodes and cathodes are localized, allowing corrosion to concentrate in certain regions (anodes). The former type of corrosion is referred to as micro cell corrosion, and the latter type of corrosion as macro cell corrosion. The type of corrosion which is often responsible for extensive damage to seawater pumps is the macro cell corrosion which includes bimetallic corrosion and differential aeration corrosion. The cathode in a macro cell is inhibited from corroding because only a cathode current flows in the cathode. Cathodic corrosion prevention is a corrosion prevention process which positively uses such a corrosion inhibiting phenomenon.

Each of systems of macro cell corrosion and cathodic corrosion prevention may be considered as a cell comprising an anode and a cathode disposed across an electrolyte. A potential ($\phi$) distribution in the electrolyte is governed by the following Laplace's equation (3):

$$\nabla^2 \phi = 0 \tag{3}$$

It is assumed that, as shown in FIG. 1 of the accompanying drawings, an electrolyte is surrounded by boundaries $\Gamma_1$, $\Gamma_2$, $\Gamma_{3a}$, and $\Gamma_{3c}$. The boundary $\Gamma_1$ is a boundary where the value of a potential $\phi$ is set to $\phi_0$, i.e., a boundary where the potential is constant. The boundary $\Gamma_2$ is a boundary where the value of a current density q is set to $q_0$, i.e., a boundary where the current density is constant. The boundaries $\Gamma_{3a}$ and $\Gamma_{3c}$ are the surface of an anode and the surface of a cathode, respectively. Boundary conditions in the respective boundaries are given by the following equations (4)–(7):

$$\text{On } \Gamma_1: \phi = \phi_0 \tag{4}$$

$$\text{On } \Gamma_2: q\{\equiv \kappa \partial \phi/\partial n\} = q_0 \tag{5}$$

$$\text{On } \Gamma_{3a}: \phi = -f_a(q) \tag{6}$$

$$\text{On } \Gamma_{3c}: \phi = -f_c(q) \tag{7}$$

where $\kappa$ represents the electric conductivity of the electrolyte, $\partial/\partial n$ a differential in the direction of an outward normal line, and $f_a(q)$ and $f_c(q)$ nonlinear functions indicative of polarization characteristics of the anode and the cathode, respectively, the nonlinear functions being determined by way of experimentation. By solving the equation (3) under the boundary conditions (4)–(7), it is possible to determine a potential distribution and a current density distribution near the surface. The potential $\phi$ and an actually measured electrode potential E are related to each other by $\phi = -E$.

Analysis According to the Boundary Element Method

According to the normal formulation of the boundary element method, the following boundary integration equation (8) is derived from the equation (3):

$$c\kappa\phi = \int_\Gamma \phi^* q \, d\Gamma - \int_\Gamma \phi q^* \, d\Gamma \tag{8}$$

where $\phi^*$ represents the fundamental solution of a three-dimensional Laplace's equation, $$q^* = \kappa \partial \phi/\partial n,$$

$\Gamma$ represents a boundary ($=\Gamma_1+\Gamma_2+\Gamma_{3a}+\Gamma_{3c}$) surrounding the electrolyte, and c is c=½ for a smooth boundary and c=$\omega/2\pi$ at an angle point of an angle $\omega$.

For numerically solving the above boundary integration equation, it is necessary to discretize the boundary integration equation. Specifically, the boundary is divided into a number of elements, and the potential $\phi$ and the current density q are approximated by a discrete value and an interpolating function at each node, providing the following simultaneous algebraic equations:

$$[A]\begin{Bmatrix} x_j \\ q_j \end{Bmatrix} = [B]\begin{Bmatrix} b_j \\ f_j(q_j) \end{Bmatrix} \tag{9}$$

where $b_j$ (j=1, 2, . . . , p) represents the value of a known component of $\phi$ or q, $x_j$ (j=1, 2, . . . , p) an unknown quantity corresponding to $b_j$, $f_j(q_j)$ (j=1, 2, . . . , s) a nonlinear function indicative of polarization characteristics, and [A] and [B] matrixes determined by the geometrical shape of the boundary $\Gamma$. Since the above equations are nonlinear, repetitive calculations are needed to solve these equations. The inventors of the present application employ the Newton-Raphson method.

Analytic Method for Axially Symmetric Region

Many actual devices to be analyzed, such as pipes and some pump components, include axially symmetric regions, and it is desirable to analyze those axially symmetric regions simply. Primarily, the following two processes are considered as effective to solve axially symmetric problems:

(i) A process which uses a fundamental solution to an axially symmetric problem; and (ii) A process which uses an ordinary fundamental solution to a three-dimensional problem and reduces the number of elements in view of axially symmetry upon discretization.

The former process of using a fundamental solution which satisfies the axially symmetric condition is problematic in that it involves more complex integrating calculations than the process of using an ordinary fundamental solution. According to the present invention, the latter process of reducing the number of elements in view of axially symmetry upon discretization is employed. This process will now be described below.

For an ordinary three-dimensional analysis, it is necessary to divide all boundaries into elements in order to discretize the boundary integration equation (8). Since $\phi$ and q have the same value in the circumferential direction owing to the axial symmetry, the boundary integration equation (8) can be modified as follows:

$$\kappa c \phi = \int_{\Gamma_{1D}} \left( q \int_0^{2\pi} r\phi^* d\theta - \phi \int_0^{2\pi} rq^* d\theta \right) d\Gamma \tag{10}$$

where $\Gamma_{1D}$ represents a range on a one-dimensional line. From the equation (10), it can obtain simultaneous algebraic equations by discretizing only $\Gamma_{1D}$. Therefore, using the axial symmetry, it is possible to greatly reduce the number of unknowns and expect an increase in the accuracy.

Process of Dividing a Region

For the sake of brevity, an area made up of two regions as shown in FIG. 2 of the accompanying drawings is considered. If an inner boundary plane is indicated by $\Gamma_B$, then since the equations (9) are satisfied in each of the regions, the following equations are satisfied:

$$\text{For the region I, } [A^I G^{IB}]\begin{Bmatrix} X^I \\ q^{IB} \end{Bmatrix} = [B^I H^{IB}]\begin{Bmatrix} b^I \\ \phi^{IB} \end{Bmatrix} \tag{11}$$

$$\text{For the region II, } [A^{II} G^{IIB}]\begin{Bmatrix} X^{II} \\ q^{IIB} \end{Bmatrix} = [B^{II} H^{IIB}]\begin{Bmatrix} b^{III} \\ \phi^{IIB} \end{Bmatrix} \tag{12}$$

where I, II represent quantities relative to the respective regions I, II, B a quantity relative to the inner boundary surface $\Gamma_B$, $\{X^M\}$ (M=I, II) a vector having a component which is a quantity relative to a boundary other than $\Gamma_B$ of $x_i$ and $q_i$, and $\{b_M\}$ (M=I, II) a vector having a component which is a known quantity (or a function indicative of a polarization curve) corresponding to $X^M$.

Inasmuch as the potential and the current density are continuous in the inner boundary, the following equations are satisfied:

$$\phi^{IB} = \phi^{IIB} \tag{13}$$

$$q^{IB} = -q^{IIB} \tag{14}$$

Transposing $[H^{MB}]\{\phi^{MB}\}$ (M=I, II) from the right-hand side to the left-hand side in the equations (11), (12), and substituting the equations (13), (14) in the resulting equations, the following equations are produced:

$$[A^I G^{IB} - H^{IB}] \begin{Bmatrix} X^I \\ q^{IB} \\ \phi^{IB} \end{Bmatrix} = [B^I]\{b^I\} \quad (15)$$

$$[-G^{IIB} - H^{IIB} A^{II}] \begin{Bmatrix} q^{IIB} \\ \phi^{IIB} \\ X^{II} \end{Bmatrix} = [B^{II}]\{b^{II}\} \quad (16)$$

These equations can be put together into the following equation (17):

$$\begin{bmatrix} A^I & G^{IB} & -H^{IB} & 0 \\ 0 & -G^{IIB} & -H^{IIB} & A^{II} \end{bmatrix} \begin{Bmatrix} X^I \\ q^{IB} \\ \phi^{IB} \\ X^{II} \end{Bmatrix} = \begin{bmatrix} B^I & 0 \\ 0 & B^{II} \end{bmatrix} \begin{Bmatrix} b^I \\ b^{II} \end{Bmatrix} \quad (17)$$

As with the equations (9), the equation (17) constitutes a nonlinear equation. According to the present invention, a solution to the equation (17) is determined by the Newton-Raphson method.

The inventors have developed six programs for analyzing an open region (such as an outer vessel surface surrounded by an electrolyte extending infinitely) and a closed region (such as an inner pump surface surrounding by an electrolyte extending in a limited space) with respect to each of two- and three-dimensional axially symmetric structures for the purpose of practically solving corrosion and corrosion prevention problems.

In an actual system, some of six regions that can be modeled two-dimensionally (open and closed regions), three-dimensionally (open and closed regions), and axially symmetrically (open and closed regions) may exist continuously. FIG. 3 of the accompanying drawings shows a specific example. In FIG. 3, a seawater pump 10 made of stainless steel has three annular sacrificial anodes 11a, 11b, 11c of Zn disposed circumferentially on an inner pump surface and four prismatic sacrificial anodes 12 of Zn disposed on an outer pump surface at equally spaced locations. The inner and outer pump surfaces communicate with each other through seawater, so that the inner pump surface should electrochemically affect the outer pump surface, and the outer pump surface should electrochemically affect the inner pump surface. Since the seawater surrounding the outer pump surface occupies a wide region, and a boundary to be divided into elements is too large for the region to be handled as a closed region, it is practically impossible to model and analyze the outer pump surface as a three-dimensional closed region like the inner pump surface.

For this reason, the inner pump surface is analyzed as a three-dimensional closed region, and the pump outer surface is analyzed as an open region. An inner surface of a guide casing is compartmented into seven flow passages by seven helical guide vanes. Since these flow passages are symmetrical in shape, one of them is removed, and divided into three-dimensional elements. Assuming that the prismatic anodes on the outer pump surface are regarded as web-shaped anodes having the same area, they are handled as axially symmetric anodes, and hence as axially symmetric models in the open region.

FIG. 4 of the accompanying drawings shows by way of example a plurality of elements divided from the outer pump surface for an axially symmetric analysis of the open region. Inasmuch as the inner and outer pump surfaces electro- chemically affect each other in reality as described above, the analysis needs to take such an electrochemically effect into consideration. However, because those regions are handled by different analyzing programs, i.e., the outer pump surface is handled by a program for the three-dimensional closed region and the inner pump surface by a program for the axially symmetric closed region, it has heretofore been impossible to analyze the inner and outer pump surfaces while taking the mutual electrochemically effect into consideration. The region dividing process developed by the inventors has been able to analyze regions modeled according to the same modeling principle.

If the process of analyzing different regions in a related fashion is applied to a situation where three-dimensional and axially symmetric regions are present continuously, then it is necessary to determine a region where the axially symmetric analysis is applicable. However, experiences and skills have to be relied upon to determine such a region because there is no process available at present for quantitatively determining the region.

SUMMARY OF THE INVENTION

It is therefore an object of the present invention to provide a method of analyzing corrosion and corrosion prevention in two or more continuous regions of one or different types in a related fashion, among those regions which are modeled two-dimensionally (open and closed regions), three-dimensionally (open and closed regions), and axially symmetrically (open and closed regions).

Another object of the present invention is to provide a method of analyzing corrosion and corrosion prevention in a situation where three-dimensional and axially symmetric regions are present continuously by determining quantitatively a region where continuous analysis of both regions is applicable.

According to an aspect of the present invention, there is provided a method of analyzing corrosion and corrosion prevention of an object, comprising the steps of dividing an object to be analyzed into a plurality of adjacent regions of plural types by a dividing plane, with one of the adjacent regions being referred to as an attentional region with a boundary as the dividing plane and the other as a non-attentional region with a boundary as the dividing plane, imparting an initial current density or an initial potential to each element of the boundary of the non-attentional region to effect a boundary element analysis for determining a relationship between a potential and a current density in each element, determining a potential distribution and a current density distribution in the attentional region in its entirety, using the relationship between the potential and the current density in each the element of the boundary of the non-attentional region as a boundary condition for the attentional region, and effecting an element analysis on the non-attentional region to determine a potential distribution and a current density distribution in the non-attentional region in its entirety, using the relationship between the potential and the current density in each element of the boundary of the attentional region as a boundary condition for the non-attentional region, whereby a potential distribution and a current density distribution across the regions can continuously be analyzed.

According to an aspect of the present invention, there is also provided a method of analyzing corrosion and corrosion prevention of an object including continuous regions which can be modeled three-dimensionally (open and closed regions) and axially symmetrically (open and closed regions), comprising the steps of extracting a candidate region which is axially symmetric, modeling the extracted region into a pipe having a radius R at a dividing plane A, imparting a current density distribution expressed by a delta function having an intensity a to the modeled pipe at r=R on a plane z=0, analytically determining a potential φ in the pipe, and determining a position z where the magnitude of a change of the potential φ is smaller than an allowable value to determine a region which can be modeled axially symmetrically. The method may further comprise the steps of dividing the object into a plurality of adjacent regions of plural types by a dividing plane, with one of the adjacent regions being referred to as an attentional region with a boundary as the dividing plane and the other as a non-attentional region with a boundary as the dividing plane, imparting an initial current density or an initial potential to each element of the boundary of the non-attentional region to effect a boundary element analysis for determining a relationship between a potential and a current density in each the element, determining a potential distribution and a current density distribution in the attentional region in its entirety, using the relationship between the potential and the current density in each the element of the boundary of the non-attentional region as a boundary condition for the attentional region, and effecting an element analysis on the non-attentional region to determine a potential distribution and a current density distribution in the non-attentional region in its entirety, using the relationship between the potential and the current density in each element of the boundary of the attentional region as a boundary condition for the non-attentional region, whereby a potential distribution and a current density distribution across the regions can continuously be analyzed.

The regions of plural types may include regions which can be modeled in two-dimensional, three-dimensional, and axially symmetric open and closed spaces.

The initial current density or the initial potential imparted to each element of the boundary of the non-attentional region may be uniform.

The regions may include at least two non-attentional regions present contiguously to one attentional region.

The above and other objects, features, and advantages of the present invention will become apparent from the following description when taken in conjunction with the accompanying drawings which illustrate preferred embodiments of the present invention by way of example.

BRIEF DESCRIPTION OF THE DRAWINGS

FIG. 2 is a diagram schematically illustrative of a process of dividing an area into two regions;

FIG. 3 is a cross-sectional view of a seawater pump to be analyzed for corrosion and corrosion prevention;

FIG. 4 is a diagram showing a plurality of elements divided from an outer pump surface for an axially symmetric analysis of an open region;

FIGS. 8A and 8B are views showing the manner in which an object to be analyzed is divided into regions.

DETAILED DESCRIPTION OF THE PREFERRED EMBODIMENTS

Figure 1:
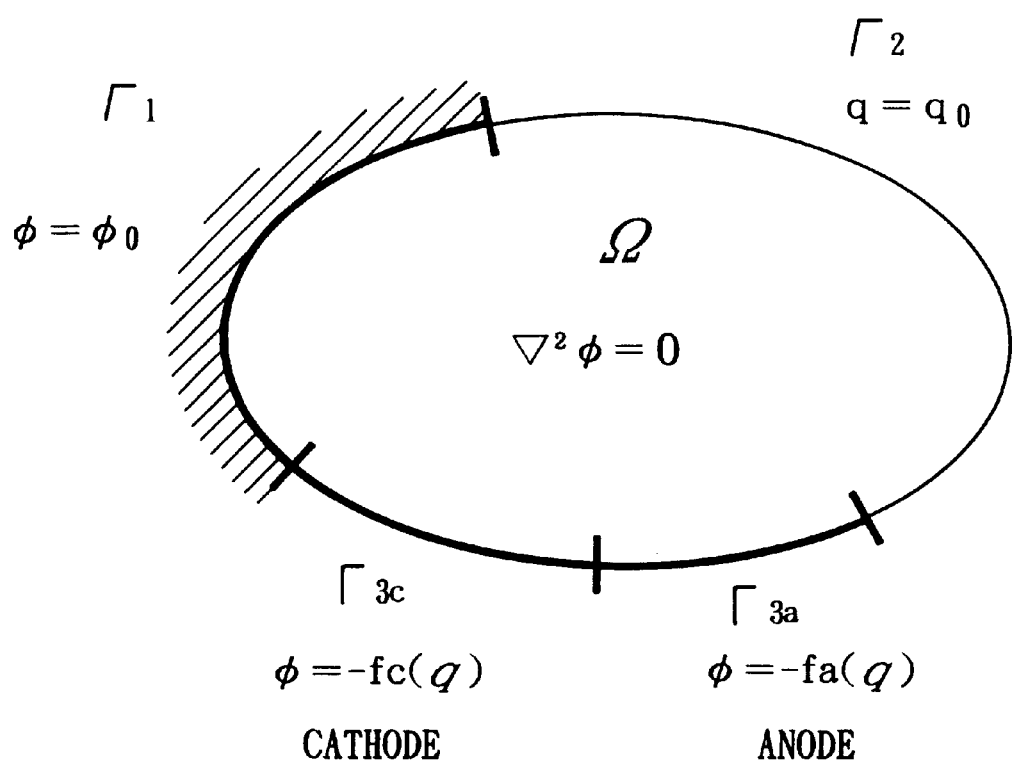
FIG. 1 is a diagram schematically illustrative of boundary conditions to determine a potential or current density distribution.
Figure 1:
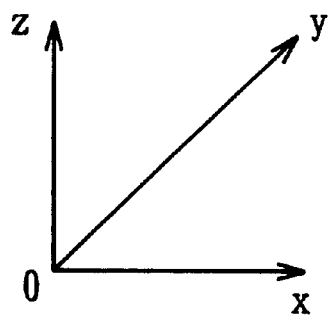
Figure 5:
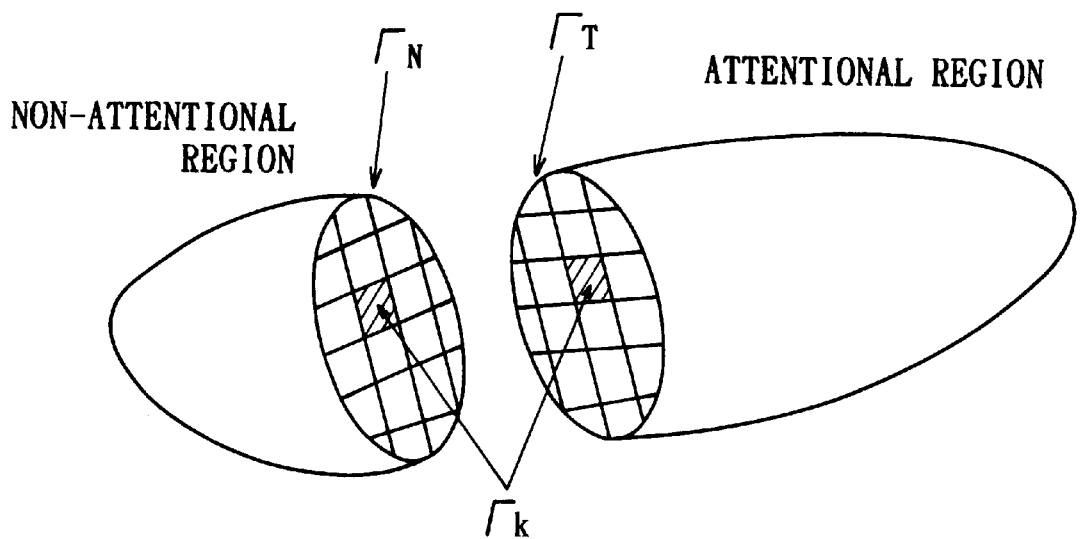
FIG. 5 is a diagram schematically illustrative of a method of analyzing corrosion and corrosion prevention according to an embodiment of the present invention.

FIG. 5 schematically illustrates a situation where two regions are continuously present. One of the regions is referred to as an attentional region and the other as a non-attentional region. The two regions are divided by a dividing plane which is referred to as a boundary $\Gamma_T$ viewed from the attentional region and as a boundary $\Gamma_N$ viewed from the non-attentional region.

A uniform current density q is imparted to each element $\Gamma_k$ of the boundary $\Gamma_N$ of the non-attentional region, and the non-attentional region is analyzed according to a boundary element process to determine a potential $\phi_k$ in each element $\Gamma_k$ of the boundary $\Gamma_N$. A uniform current density $q_a$ is imparted to each element $\Gamma_k$ of the boundary $\Gamma_N$, and a potential response $\phi_{ak}$ is determined at this time. Since the equation $\phi_{ak}=f_k(q_a)$ between the current density and the potential in each element $\Gamma_k$ of the boundary $\Gamma_N$ is also applicable to the boundary $\Gamma_T$ viewed from the attentional region, it is used as a boundary condition on the boundary $\Gamma_T$. Therefore, using this boundary condition, the attentional region can be analyzed taking the non-attentional region into account. The above relationship between the current density and the potential is referred to as an equivalent boundary condition. If the non-attentional region is analyzed again using a current density or a potential on the boundary $\Gamma_T$ which is obtained from the analysis of the attentional region, then the two continuous regions can be analyzed in their entirety. For analyzing the non-attentional region, a uniform potential, rather than the uniform current, may be imparted as an initial condition to the non-attentional region. The initial current density or potential to be imparted to the non-attentional region may not necessarily be uniform, but may differ slightly from element to element.

Figure 6:
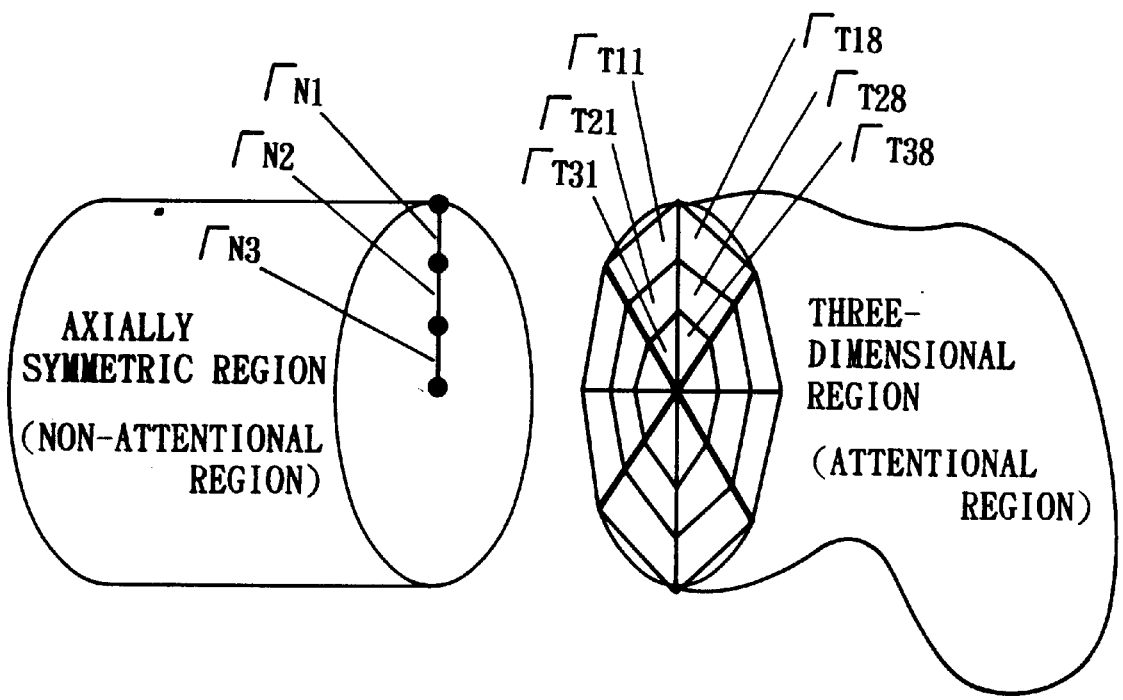
FIG. 6 is a diagram showing an example in which a region shown in FIG. 5 is divided into elements.

FIG. 6 specifically shows an example in which an axially symmetrical region and a region that can be modeled three-dimensionally are present continuously. In this example, it is preferable that a non-attentional region which needs to be analyzed a plurality of times with different potentials or current densities should be the axially symmetrical region that requires a shorter analyzing time. The relationship between a potential and a current density on elements $\Gamma_{N1}, \Gamma_{N2}, \Gamma_{N3}$ obtained by an analysis of the axially symmetrical region is used as a boundary condition for corresponding elements $\Gamma_{A11}-\Gamma_{A18}, \Gamma_{A21}-\Gamma_{A28}, \Gamma_{A31}-\Gamma_{A38}$ of the three-dimensionally modeled region.

Figure 7:
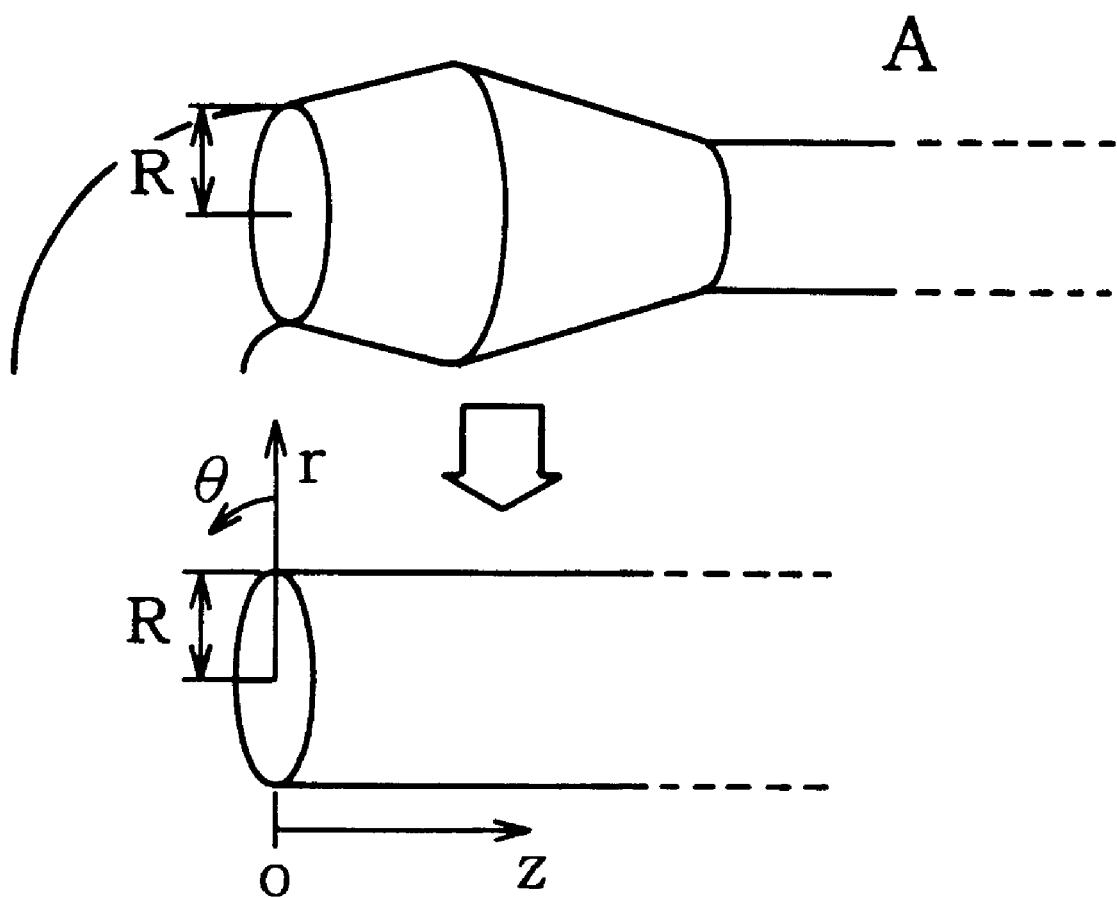
FIG. 7 is a diagram schematically illustrative of a method of analyzing corrosion and corrosion prevention according to another embodiment of the present invention.

According to the present invention, a region that can be molded axially symmetrically, i.e., a region to which axially symmetric elements are quantitatively applied, is determined using an analytic solution to the Laplace's equation governing corrosion problems. As shown in FIG. 7, a symmetric member of a complex-shape device is extracted, and the extracted member is modeled into a pipe having a radius R at a dividing plane A. A current density distribution expressed by a delta function having an intensity a is imparted to the modeled pipe at r=R on a plane z=0, and a potential φ in the pipe is analytically determined at this time. If it is assumed that polarization characteristics in the pipe are expressed by $\phi=-(ki+\phi_0)$ (i represents the current density), then the analytic solution of the potential in the pipe is given as follows:

$$\phi(r, \theta, z) = \sum_{l=0}^{\infty} \sum_{m=1}^{\infty} C_{lm} J_l(q_{lm} R)\cos(l\theta) e^{-q_{lm} z} - \phi_0 \quad (18)$$

$$J_{|l|}(q_{lm} R) + k q_{lm} J'_{|l|}(q_{lm} R) = 0 \quad (19)$$

$$C_{lm} = \begin{cases} \dfrac{a J_l(q_{lm} R)}{2\pi k q_{lm} \int_0^R r\{J_l(q_{lm} r)\}^2 \, dr} & (l = 0) \\ \dfrac{a J_l(q_{lm} R)}{\pi k q_{lm} \int_0^R r\{J_l(q_{lm} r)\}^2 \, dr} & (l \ne 0) \end{cases} \quad (20)$$

$$\frac{\max\phi(z) - \overline{\phi}(z)}{\overline{\phi}(z)} \approx \frac{\sum_{m=1}^{3} C_{lm} J(q_{lm}) e^{-q_{lm} z}}{\sum_{m=1}^{3} C_{0m} J_0(q_{0m} R) e^{-q_{0m} z_0} - \phi_0} < \varepsilon \quad (21)$$

An example of the present invention will be described below.

An analyzed object was a vertical-shaft pump having a diameter of 200 mm and a length of 6000 mm, as shown in FIG. 8A. As shown in FIG. 8A, the pump was divided into inner portions 15, 16 and an outer portion 17. The inner portions included a guide casing 15 of complex three-dimensional shape composed of a complex assembly of parts and having a helical flow passages, and a column pipe 16 which can be modeled axially symmetrically. In order to determine a region to which axially symmetrical elements are applicable among the inner portions, calculations were made with the allowable error $\varepsilon$ in the equation (21) being set to 0.02. As a result, the region to which axially symmetrical elements are applicable was determined as being spaced 192 mm from the upper end of the guide casing 15. Therefore, an inner column pipe surface handled as an axially symmetric region was spaced 200 mm or more from the upper end of the guide casing 15. Three regions which were divided were an outer pump surface handled as an axially symmetric open region, an inner guide casing surface as a three-dimensional closed region, and an inner column pipe surface as an axially symmetric closed region. The inner guide casing surface was compartmented into seven flow passages by seven helical guide vanes. Since these flow passages were symmetrical in shape, one of them was removed, and divided into three-dimensional elements.

In order to determine an equivalent boundary condition for boundary planes $\Gamma_a$, $\Gamma_b$ between the outer pump surface, the inner column pipe surface, and the inner guide casing surface, a boundary element analysis was conducted on the outer pump surface and the inner column pipe surface. Specifically, an axially symmetric open region analysis was effected on the outer pump surface, and an axially symmetric closed region analysis was effected on the inner column pipe surface. A current density ranging from −2.0 to 2.0 A/m² was applied in increments of 0.2 A/m² to each element of the boundary planes $\Gamma_a$, $\Gamma_b$. Using the determined equivalent boundary condition, i.e., the relationship between the current density and the potential, as a boundary condition, a three-dimensional closed region analysis was carried out on the guide casing 15. Using an obtained current density at the boundary planes $\Gamma_a$, $\Gamma_b$ as a boundary condition, the outer pump surface and the inner column pipe surface were analyzed again. In this manner, all the analysis was completed. The potential distribution of the inner guide casing surface, etc. which was obtained as a result of the analysis was considered as highly close to an actual potential distribution.

Heretofore, for analyzing a situation where two or more of six regions that are modeled two-dimensionally (open and closed regions), three-dimensionally (open and closed regions), and axially symmetrically (open and closed regions) exist continuously, the regions have to be analyzed separately. According to the present invention, however, all the regions can be analyzed in a related fashion, so that a potential distribution or a current density distribution in boundaries can be determined accurately.

For example, it has been customary to separately analyze inner and outer pump surfaces of a vertical-shaft pump though they are electrochemically affected by each other, and hence the pump cannot accurately be analyzed for corrosion and corrosion prevention. According to the present invention, it is possible to analyze such inner and outer pump surfaces in a related manner. Furthermore, while the entire inner pump surface has heretofore been analyzed with a three-dimensional closed region model, it is possible according to the present invention to analyze an inner column pipe surface of simple configuration with an axially symmetric model, allowing it to be divided easily into elements.

In the case where a three-dimensional region and an axially symmetric region are existing continuously, it has conventionally been unable to determine accurately a region which can be modeled axially symmetrically. According to the present invention, however, such a region can be determined quantitatively.

The present invention has been described as being applied to a method of analyzing corrosion and corrosion prevention of metals. However, the principles of the present invention are also applicable to the plating of metals, the designing of batteries and electrolytic tanks, etc.

Although certain preferred embodiments of the present invention have been shown and described in detail, it should be understood that various changes and modifications may be made therein without departing from the scope of the appended claims.

What is claimed is:

1. A method of predicting corrosion and corrosion prevention of an object, comprising the steps of:

selecting an object having three dimensional structure to be analyzed, said object being made of metal and used in a solution having electric conductivity;

dividing said object into a plurality of adjacent regions of plural types by a dividing plane, with one of the adjacent regions being referred to as an attentional region with a boundary as said dividing plane and the other as a non-attentional region with a boundary as said dividing plane;

imparting a current to produce an initial current density or an initial potential to each element of the boundary of the non-attentional region to effect a boundary element analysis for determining a relationship between a potential and a current density in each said element;

determining a potential distribution and a current density distribution in said attentional region in its entirety, using said relationship between the potential and the current density in each said element of the boundary of the non-attentional region as a boundary condition for the attentional region, whereby the boundary condition for the attentional region is equal to a boundary condition of the non-attentional region;

effecting an element analysis on said non-attentional region to determine a potential distribution and a current density distribution in said non-attentional region in its entirety, using said relationship between the potential and the current density in each element of the boundary of the attentional region as a boundary condition for the non-attentional region, thereby a potential distribution and a current density distribution across the regions can continuously be analyzed; and using said potential distribution and said current density distribution for predicting corrosion and corrosion prevention of said object.

2. A method according to claim 1, wherein said regions of plural types include regions which can be modeled in two-dimensional, three-dimensional, and axially symmetric open and closed spaces.

3. A method according to claim 2, further comprising the steps of:

extracting a candidate region which is axially symmetric;

modeling the extracted region into a pipe having a radius R at a dividing plane A;

imparting a current density distribution expressed by a delta function having an intensity a to the modeled pipe at r=R on a plane z=0;

analytically determining a potential $\phi$ in the pipe; and determining a position z where the magnitude of a change of the potential $\phi$ is smaller than an allowable value to determine a region which can be modeled axially symmetrically.

4. A method according to claim 1, wherein said initial current density or said initial potential imparted to each element of the boundary of the non-attentional region is uniform.

5. A method according to claim 1, wherein said regions include at least two non-attentional regions present contiguously to one attentional region.

* * * * *